United States Patent [19]

Stevenson

[11] Patent Number: 5,728,693
[45] Date of Patent: Mar. 17, 1998

[54] ARTHROPODICIDAL OXADIAZINE-THIADIAZINE- OR TRIAZINE-CARBOXANILIDES

[75] Inventor: Thomas Martin Stevenson, Newark, Del.

[73] Assignee: E. I. du Pont de Nemours and Company, Wilmington, Del.

[21] Appl. No.: 666,499

[22] PCT Filed: Dec. 21, 1994

[86] PCT No.: PCT/US94/14241

§ 371 Date: Jun. 25, 1996

§ 102(e) Date: Jun. 25, 1996

[87] PCT Pub. No.: WO95/18116

PCT Pub. Date: Jul. 6, 1995

Related U.S. Application Data

[63] Continuation-in-part of Ser. No. 175,843, Dec. 29, 1993, abandoned.

[51] Int. Cl.$^6$ .................... C07D 273/04; A01N 43/88
[52] U.S. Cl. .................... 514/229.2; 544/66; 544/68; 544/73; 544/70; 544/69; 544/32; 544/34; 544/14; 544/9; 544/6; 514/222.8; 514/214; 514/79; 514/80; 514/63

[58] Field of Search ................ 514/229.2, 222.8, 514/214, 79, 80, 63; 544/6, 34, 70, 68

[56] References Cited

FOREIGN PATENT DOCUMENTS

WO91/17983  11/1991  WIPO.
WO92/11249  7/1992  WIPO.
93/19045  9/1993  WIPO.

*Primary Examiner*—John M. Ford

[57] ABSTRACT

Arthropodicidal compounds, compositions and use of compounds having the formula

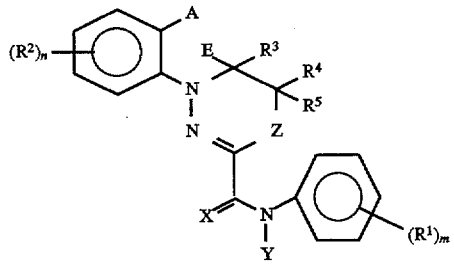

9 Claims, No Drawings

ARTHROPODICIDAL OXADIAZINE-THIADIAZINE-OR TRIAZINE-CARBOXANILIDES

CROSS-REFERENCES TO RELATED APPLICATIONS

This is a 35 U.S.C. 371 national filing of PCT/US94/14241, filed 21 Dec. 1994 which is a continuation-in-part of U.S. Ser. No. 08/175,843, filed 29 Dec. 1993, now abandoned.

The present invention comprises carboxanilides useful as arthropodicides and acaricides. WO 92/11249 pertains to insecticidal carboxanilides that do not suggest those of the instant invention.

SUMMARY OF THE INVENTION

This invention pertains to compounds of Formula I, including all geometric and stereoisomers, agriculturally suitable salts thereof, agricultural compositions containing them and their use to control arthropods in both agronomic and nonagronomic environments. The compounds are:

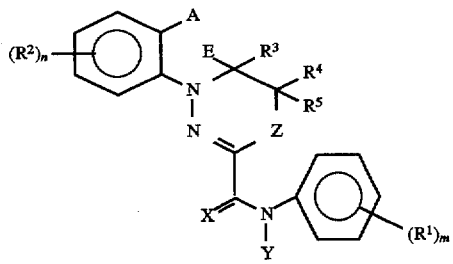

wherein:

A is H;

E is selected from the group H and $C_1-C_3$ alkyl; or

A and E are taken together to form a member selected from the group $CH_2$, $CH_2CH_2$, O, $S(O)_r$, $NR^6$, $OCH_2$, $S(O)_rCH_2$, $N(R^6)CH_2$, substituted $CH_2$, and substituted $CH_2CH_2$, the substituents independently selected from 1–2 halogen and 1–2 methyl;

X and $X^1$ are independently selected from the group O and S;

Y is selected from the group H, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_3-C_6$ cycloalkyl, $C_3-C_6$ halocycloalkyl, $C_4-C_7$ cycloalkylalkyl, CHO, $C(O)R^{14}$, $C(O)OR^{14}$, $C(S)R^{14}$, $C(S)SR^{14}$, $C(O)C(O)OR^{14}$, $C(O)CH_2C(O)OR^{14}$, $S(O)_rR^{14}$, $S(O)_2CH_2C(O)OR^{14}$, $P(X^1)(OR^{16})_2$, $S(O)_rN(R^{11})C(O)OR^{10}$, $S(O)_rN(R^{12})R^{13}$, $N=CR^8R^9$, $OR^7$, $NR^7R^8$; benzyl substituted with 1–3 substituents independently selected from W; and $C_1-C_6$ alkyl substituted with 1–3 substituents independently selected from the group $C_1-C_3$ alkoxy, $C_1-C_3$ haloalkoxy, CN, $NO_2$, $S(O)_rR^{14}$, $P(X^1)(OR^{16})_2$, $C(O)R^{14}$, $C(O)OR^{14}$ and phenyl substituted with 1–3 substituents independently selected from W;

Z is selected from the group O, $S(O)_r$ and $NR^{17}$;

$R^1$ and $R^2$ are independently selected from the group H, halogen, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $OR^7$, $C_2-C_6$ alkoxyalkyl, $C_2-C_6$ alkylthioalkyl, $C_1-C_6$ nitroalkyl, $C_2-C_6$ cyanoalkyl, $C_3-C_8$ alkoxycarbonylalkyl, $C_3-C_6$ cycloalkyl, $C_3-C_6$ halocycloalkyl, CN, $N_3$, SCN, $NO_2$, SH, $S(O)_rR^{14}$, OCHO, CHO, $C(O)R^{14}$, $C(O)OR^{14}$, $C(O)NR^{14}R^{15}$, $S(O)_2NR^{14}R^{15}$, $NR^{14}R^{15}$, $NR^{15}C(O)R^{14}$, $OC(O)NHR^{14}$, $NR^{15}C(O)NHR^{14}$, $NR^{15}S(O)_2R^{14}$, $SF_5$, phenyl substituted with 1–3 substituents independently selected from W, and benzyl substituted with 1–3 substituents independently selected from W; or when m or n is 2 and the two $R^1$ groups or the two $R^2$ groups are adjacent, $(R^1)_2$ or $(R^2)_2$ are taken together as $-OCH_2O-$, $-OCF_2O-$, $-OCH_2CH_2O-$, $-CH_2C(CH_3)_2O-$, $-CF_2CF_2O-$ or $-OCF_2CF_2O-$ to form a cyclic bridge;

$R^3$ is selected from the group J, H, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_3-C_6$ cycloalkyl, $C_4-C_7$ cycloalkylalkyl, $OR^7$, $C_3-C_8$ alkoxycarbonylalkyl, CHO, $C(O)R^{14}$, $C(O)OR^{14}$, $C(O)NR^{14}R^{15}$, $C(S)NR^{14}R^{15}$, $C(S)R^{14}$, $C(S)SR^{14}$, CN, $Si(R^{18})(R^{19})(R^{20})$, $S(O)_rR^{14}$, $P(X^1)(OR^{16})_2$, $NR^7R^8$, phenyl substituted with $(R^{21})_p$, and benzyl substituted with 1–3 substituents independently selected from W; or $R^3$ is $C_2-C_6$ epoxyalkyl optionally substituted with 1–2 substituents independently selected from the group $C_1-C_3$ alkyl, CN, $C(O)R^{14}$, $C(O)OR^{14}$ and phenyl substituted with 1–3 substituents independently selected from W; or $R^3$ is $C_1-C_6$ alkyl substituted with 1–3 substituents independently selected from the group $OR^7$, $C(O)NR^{14}R^{15}$, $C(O)R^{14}$, $S(O)_rR^{14}$, SCN, CN, $C_1-C_2$ haloalkoxy, $Si(R^{18})(R^{19})(R^{20})$ and $NR^7R^8$;

$R^4$ and $R^5$ are independently selected from the group H and $C_1-C_4$ alkyl;

$R^6$ is selected from the group H, $C_1-C_4$ alkyl, $C_1-C_4$ haloalkyl, $C_2-C_4$ alkenyl, $C_2-C_4$ haloalkenyl, $C_2-C_4$ alkynyl, $C_2-C_4$ haloalkynyl, CHO, $C(O)R^{14}$, $C(O)OR^{14}$, $C(O)NR^{14}R^{15}$, $C(S)NR^{14}R^{15}$, $C(S)R^{14}$, $C(S)SR^{14}$, $S(O)_rR^{14}$, $P(X^1)(OR^{16})_2$, substituted phenyl, and substituted benzyl wherein the phenyl and benzyl substituents are 1–3 substituents independently selected from W;

$R^7$ is selected from the group H, $C_1-C_4$ alkyl, $C_1-C_4$ haloalkyl, $C_2-C_4$ alkenyl, $C_2-C_4$ haloalkenyl, $C_2-C_4$ alkynyl, $C_2-C_4$ haloalkynyl, $C(O)R^{14}$, $C(O)OR^{14}$, $C(O)NR^{14}R^{15}$, $S(O)_2NR^{14}R^{15}$, $S(O)_2R^{14}$, substituted phenyl, and substituted benzyl wherein the phenyl and benzyl substituents are 1–3 substituents independently selected from W;

$R^8$ is selected from the group H, $C_1-C_4$ alkyl, $C(O)R^{14}$ and $C(O)OR^{14}$;

$R^9$ is selected from the group H, $C_1-C_4$ alkyl, $C_1-C_4$ haloalkyl and phenyl substituted with 1–3 substituents independently selected from W; or $R^8$ and $R^9$ are taken together as $(CH_2)_4$ or $(CH_2)_5$;

$R^{10}$ is $C_1-C_{18}$ alkyl;

$R^{11}$ is $C_1-C_4$ alkyl;

$R^{12}$ and $R^{13}$ are independently $C_1-C_4$ alkyl; or $R^{12}$ and $R^{13}$ are taken together as $(CH_2)_4$, $(CH_2)_5$ or $CH_2CH_2OCH_2CH_2$;

$R^{14}$ is selected from the group $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_2-C_6$ alkoxyalkyl, $C_2-C_6$ alkylthioalkyl, $C_1-C_6$ nitroalkyl, $C_2-C_6$ cyanoalkyl, $C_3-C_8$ alkoxycarbonylalkyl, $C_3-C_6$ cycloalkyl, $C_3-C_6$ halocycloalkyl, $C_4-C_7$ cycloalkylalkyl, substituted phenyl and substituted benzyl wherein the phenyl and benzyl substituents are 1–3 substituents independently selected from W;

$R^{15}$ is selected from the group H and $C_1-C_4$ alkyl; or $R^{14}$ and $R^{15}$, when attached to the same atom, are taken together as $(CH_2)_4$, $(CH_2)_5$ or $CH_2CH_2OCH_2CH_2$;

$R^{16}$ is selected from the group $C_1-C_3$ alkyl and phenyl substituted with 1–3 substituents independently selected from W;

$R^{17}$ is selected from the group H, $C_1-C_6$ alkyl, $C_1-C_6$ haloalkyl, $C_2-C_6$ alkenyl, $C_2-C_6$ halo alkenyl, $C_2-C_6$ alkynyl, $C_2-C_6$ haloalkynyl, $C_3-C_6$ cycloalkyl, $C_3-C_6$ halocycloalkyl, $C_4-C_7$ cycloalkylalkyl, CHO, $C(O)R^{14}$, C(O)OR$^{14}$, C(S)R$^{14}$, C(S)SR$^{14}$, C(O)C(O)OR$^{14}$, C(O)CH$_2$C(O)OR$^{14}$, S(O)$_r$R$^{14}$, S(O)$_2$CH$_2$C(O)OR$^{14}$, P(X$^1$)(OR$^{16}$)$_2$, C(O)NR$^{14}$R$^{15}$, S(O)$_r$NR$^{14}$R$^{15}$, S(O)$_r$N(R$^{11}$)C(O)OR$^{10}$, S(O)$_r$N(R$^{11}$)CHO, C(O)Ph where the phenyl group is substituted by 1–2 substituents independently selected from W, and benzyl substituted by 1–2 substituents independently selected from W; or R$^{17}$ is C$_1$–C$_4$ alkyl substituted with 1–2 substituents independently selected from C$_1$–C$_2$ alkoxy, C$_1$–C$_2$ haloalkoxy, CN, NO$_2$, C(O)R$^{14}$, C(O)OR$^{14}$ and NR$^7$R$^8$;

R$^{18}$ and R$^{19}$ are independently C$_1$–C$_4$ alkyl;

R$^{20}$ is selected from the group C$_1$–C$_4$ alkyl and phenyl substituted with 1–2 substituents independently selected from W;

R$^{21}$ is selected from the group C$_1$–C$_6$ alkyl, C$_1$–C$_6$ haloalkyl, C$_2$–C$_6$ alkenyl, C$_2$–C$_6$ haloalkenyl, C$_2$–C$_6$ alkynyl, C$_2$–C$_6$ haloalkynyl, OH, OR$^{14}$, C$_2$–C$_6$ alkoxyalkyl, C$_2$–C$_6$ alkylthioalkyl, C$_1$–C$_6$ nitroalkyl, C$_2$–C$_6$ cyanoalkyl, C$_3$–C$_8$ alkoxycarbonylalkyl, C$_3$–C$_6$ cycloalkyl, C$_3$–C$_6$ halocycloalkyl, halogen, CN, N$_3$, SCN, SF$_5$, NO$_2$, CHO, C(O)R$^{14}$, C(O)OR$^{14}$, C(O)NR$^{14}$R$^{15}$, S(O)$_r$R$^{14}$, OC(O)R$^{14}$, OC(O)OR$^{14}$, OS(O)$_2$R$^{14}$, S(O)$_2$NR$^{14}$R$^{15}$, NR$^{14}$R$^{15}$, NR$^{15}$C(O)R$^{14}$, OC(O)NHR$^{14}$, NR$^{15}$C(O)NHR$^{14}$, NR$^{15}$S(O)$_2$R$^{14}$, phenyl substituted with 1–3 substituents independently selected from W, and benzyl substituted with 1–3 substituents independently selected from W; or when p is 2 and the two R$^{21}$ groups are adjacent, (R$^{21}$)$_2$ are optionally taken together as —OCH$_2$O—, —OCF$_2$O—, —OCH$_2$CH$_2$O—, —CH$_2$C(CH$_3$)$_2$O—, —CF$_2$CF$_2$O— or —OCF$_2$CF$_2$O— to form a cyclic bridge;

J is selected from the group

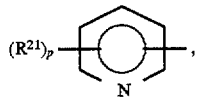
J-1

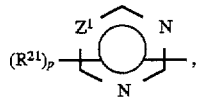
J-2

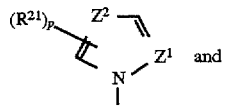
J-3 and

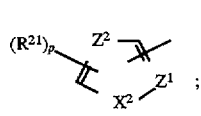
J-4;

W is selected from the group H, halogen, CN, NO$_2$, C$_1$–C$_2$ alkyl, C$_1$–C$_2$ haloalkyl, C$_1$–C$_2$ alkoxy, C$_1$–C$_2$ haloalkoxy, C$_1$–C$_2$ alkylthio, C$_1$–C$_2$ haloalkylthio, C$_1$–C$_2$ alkylsulfonyl, and C$_1$–C$_2$ haloalkylsulfonyl;

X$^2$ is selected from the group O and S;

Z$^1$ and Z$^2$ are independently selected from the group CH and N;

m is 1 to 3;

n is 1 to 3;

p is 0 to 3; and r is 0, 1 or 2.

Exemplary values of J include:

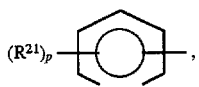
J-1

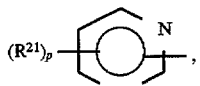
J-2(1)

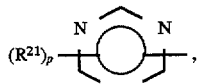
J-2(2)

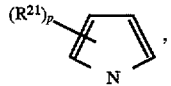
J-3(1)

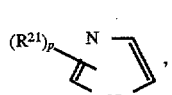
J-3(2)

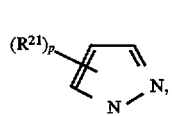
J-3(3)

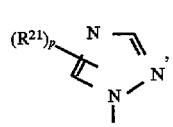
J-3(4)

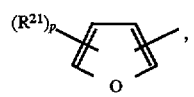
J-4(1)

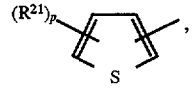
J-4(2)

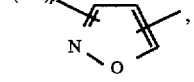
J-4(3)

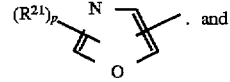
J-4(4)

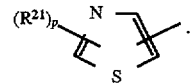
J-4(5)

Preferred Compounds A are compounds of Formula I wherein

Y is selected from the group H, C$_1$–C$_6$ alkyl, C(O)R$^{14}$ and C(O)OR$^{14}$.

Preferred Compounds B are compounds of Preferred A wherein

R$^3$ is selected from the group C$_1$–C$_4$ alkyl, C(O)OR$^{14}$ and phenyl substituted with (R$^{21}$)$_p$; and X is O.

Preferred Compounds C are compounds of Preferred B wherein $R^1$ is selected from the group $C_1$–$C_2$ haloalkyl, $C_1$–$C_2$ haloalkoxy and halogen;

$R^2$ is selected from the group H, $C_1$–$C_2$ haloalkyl, $C_1$–$C_2$ haloalkoxy and halogen;

m is 1; and n is 1.

Preferred Compounds D are compounds of Preferred C wherein

A and E are taken together to form $CH_2$ and $OCH_2$.

Preferred Compounds E are compounds of Preferred C wherein

A is H;

E is H; and $R^2$ is in the meta position.

Specifically preferred for biological activity is Compound F of Preferred E which is:

4-(3-chlorophenyl)-5,6-dihydro-5-phenyl-N-[4-(trifluoromethoxy)phenyl]-4H-1,3,4-oxadiazine-2-carboxamide.

Compounds of this invention can exist as one or more stereoisomers. The various stereoisomers include enantiomers, diastereomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate said stereoisomers. Accordingly, the present invention comprises racemic mixtures, individual stereoisomers, and optically active mixtures of compounds of Formula I as well as agriculturally suitable salts thereof.

In the above recitations, the term "alkyl", used either alone or in compound words such as "alkylthio" or "haloalkyl" denotes straight-chain or branched alkyl, such as, methyl, ethyl, n-propyl, i-propyl, or the different isomers through octadecyl. "Alkenyl" denotes straight-chain or branched alkenes such as ethenyl, 1-propenyl, 2-propenyl, and the different butenyl, pentenyl and hexenyl isomers. "Alkenyl" also denotes polyenes such as 1,3-hexadiene. "Alkynyl" denotes straight-chain or branched alkynes such as ethynyl, 1-propynyl, 3-propynyl and the different butynyl, pentynyl and hexynyl isomers. "Alkoxy" denotes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$ and the different pentyl and hexyl isomers. "Alkylthio" denotes straight-chain or branched alkylthio moieties such as methylthio, ethylthio, and the different propylthio, butylthio, pentylthio and hexylthio isomers. "Alkylthioalkyl" denotes alkylthio appended to a straight or branched-chain alkyl group. "Alkylsulfonyl" denotes $CH_3S(O)_2$ and $CH_3CH_2S(O)_2$. "Cycloalkyl" denotes, for example, cyclopropyl, cyclobutyl, cyclopentyl, and cyclohexyl. Examples of "cycloalkylalkyl" include cyclopropylmethyl, cyclopropylethyl, cyclobutylmethyl and the different $C_6$ and $C_7$ isomers bonded to straight-chain or branched alkyl groups. "Alkoxycarbonylalkyl" denotes straight-chain or branched esters substituted on straight-chain or branched alkyl groups. Examples of "alkoxycarbonylalkyl" include $CH_2C(O)OCH_3$, $CH_2C(O)OCH_2CH_3$, $CH_2CH_2C(O)OCH_3$ and the different $C_4$, $C_5$, $C_6$, $C_7$ and $C_8$ isomers. The term "halogen", either alone or in compound words such as "haloalkyl", denotes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $CF_2HCH_2CH_2O$ and $CF_3CH_2O$. Examples of "haloalkylthio" include $CCl_3S$, $CF_3S$, and $CCl_3CH_2S$. Examples of "haloalkylsulfonyl" include $CF_3SO_2$, $CCl_3SO_2$, $CF_3CH_2SO_2$ and $CF_3CF_2SO_2$. The total number of carbon atoms in a substituent group is indicated by the "$C_i$–$C_j$" prefix where i and j are numbers from 1 to 18. For example, $C_1$–$C_6$ alkyl designates methyl, ethyl, and propyl through hexyl isomers; $C_2$ alkoxy designates $CH_3CH_2O$—; and $C_3$ alkoxy designates $CH_3CH_2CH_2O$— or $(CH_3)_2CHO$—. Nitroalkyl designates a straight or branched-chain alkyl group substituted with $NO_2$. Cyanoalkyl designates a straight or branched-chain alkyl group substituted with CN.

DETAILS OF THE INVENTION

Compounds of Formula I (where Y is not H) can be prepared by the reaction of alkali amides on compounds of Formula III as shown in Scheme 1. Alkali amides can be prepared by the reaction of aluminum or magnesium reagents V with anilines of Formula IV. In a typical transformation, the aniline of Formula IV is dissolved in an inert solvent such as dichloromethane or toluene and treated with an aluminum or magnesium reagent such as trimethyl aluminum or methyl magnesium chloride. The compound of Formula III is then added and the reaction continued at a temperature of 20°–115° C. The reaction is usually complete in 2 to 24 h. The anilines of Formula IV and aluminum and magnesium reagents are generally commercially available. For further details concerning the use of alkali amides for the formation of amides see *Organic Syntheses*, 59, pp 49–53 (1980) and references cited therein.

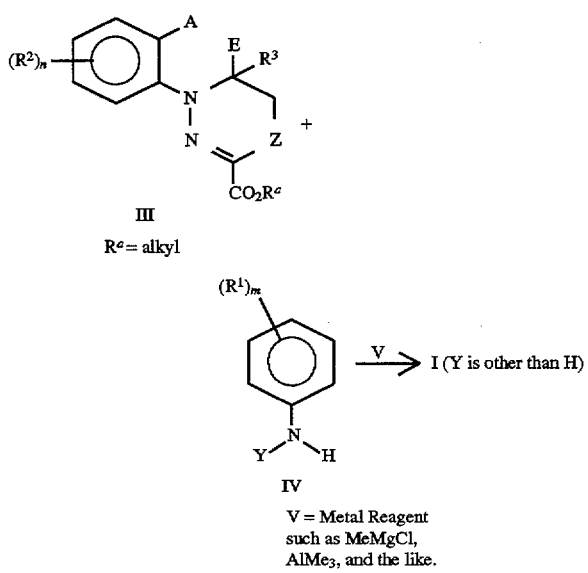

Scheme 1

V = Metal Reagent such as MeMgCl, AlMe₃, and the like.

Alternatively, as depicted in Scheme 2, compounds of Formula I (where Y is other than H) can be prepared by the reaction of compounds of Formula I (where Y is H) with compounds of Formula II in the presence of a suitable base.

Many bases can be utilized for this transformation including alkali hydrides and alkoxides, tertiary amines, and pyridine. A wide variety of solvents which are inert to the presence of base can be employed with dipolar aprotic solvents such as dimethylformamide. The reaction can be run at temperatures between about −15°–100° C., with temperatures of 0°–30° C. being preferred. The reaction is usually complete in 1 to 24 h.

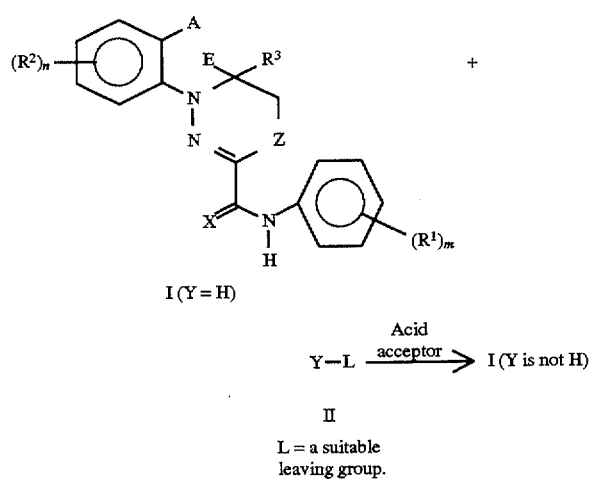

Compounds of Formula I (where Y=H) can be prepared by the reaction of alkali amides on compounds of Formula III as shown in Scheme 3. Alkali amides can be prepared by the action of aluminum or magnesium reagents V with anilines of Formula IV. In a typical transformation, the aniline of Formula IV is dissolved in an inert solvent such as dichloromethane or toluene and treated with an aluminum or magnesium reagent such as trimethyl aluminum or methyl magnesium chloride. The anilines of Formula IV and aluminum and magnesium reagents are generally commercially available. For further details concerning the use of alkali amides for the formation of amides see *Organic Syntheses*, 59, pp 49–53 (1980) and references cited therein.

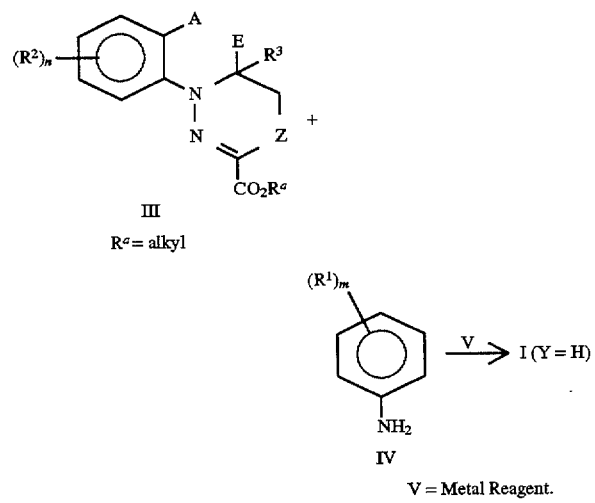

Compounds of Formula III (where A=H) can be prepared as shown in Scheme 4 by the reaction of hydrazides of Formula VI with bis-electrophiles of Formula VII in the presence of base. The reaction can be carried out in the presence of both inorganic and organic bases such as triethylamine, potassium carbonate, cesium carbonate, and potassium hydroxide. The reaction is best carried out in polar solvents such as methanol, ethanol, acetonitrile, dimethylformamide or dimethylacetamide at temperatures from 20°–165° C. The reaction is usually complete in 2 to 18 h. Formula VII compounds are dibromides which are commercially available or can be readily prepared by bromination of commercially available olefins through known procedures.

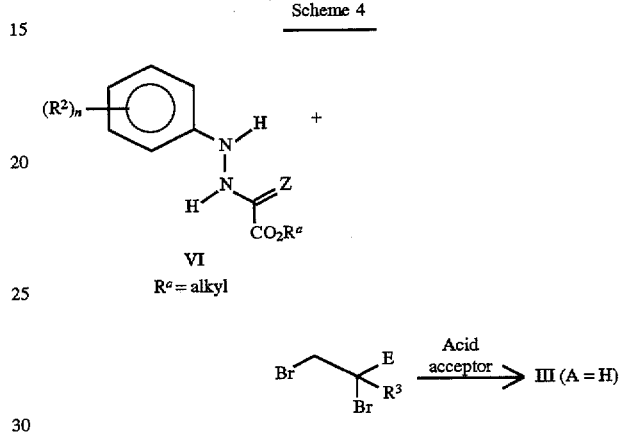

Alternatively, compounds of Formula III (A=H) can be prepared by reaction of azocompounds of Formula VIII with substituted alkenes of Formula IX as shown in Scheme 5. The hetero Diels-Alder reaction of hetero-1,2-diaza-1,3-butadienes related to compound VIII is known and has been reviewed (Hetero Diels-Alder Methodology in *Organic Synthesis*, Boger and Weinreb editors, Academic Press, San Diego, (1987), pp 270°–271). The reaction can be carried out in various solvents, and aromatic hydrocarbons such as toluene and xylenes are preferred. The reaction can be carried out at temperatures from 20°–150° C.

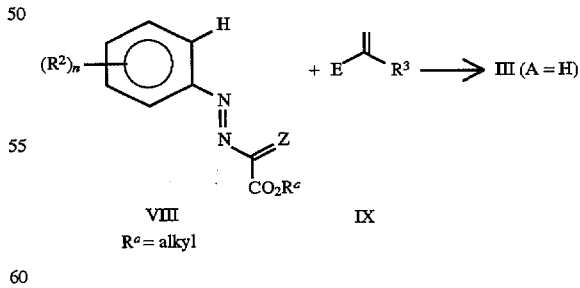

Similarly, as depicted in Scheme 6, compounds of Formula III (where A and E are taken together to form a ring) can be prepared by reacting the azo-alkene compound of Formula X under the conditions described in Scheme 5.

Scheme 6

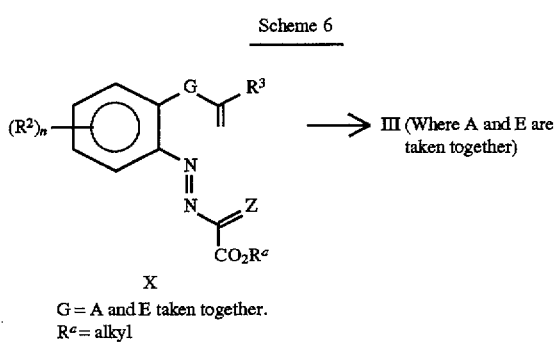

G = A and E taken together.
$R^a$ = alkyl

Scheme 8

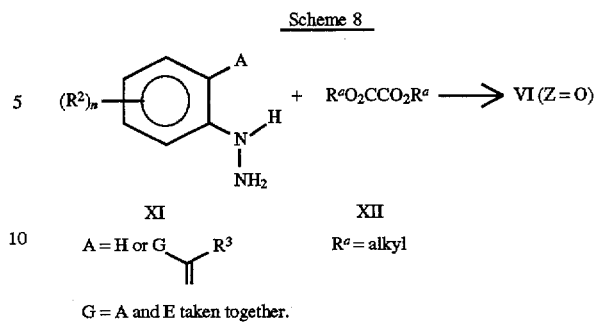

A = H or G $\underset{\|}{\overset{R^3}{\diagdown}}$ $R^a$ = alkyl

G = A and E taken together.

The compounds of Formulae VIII and X can be made by the oxidation of compounds of Formula VI by the method depicted in Scheme 7. The transformation of hydrazides to azo compounds is known in the art and can be accomplished with a wide variety of oxidants. Metal salts such as ferric chloride, peroxides such as hydrogen peroxide, halogens such as bromine, and metals such as palladium in the presence of air can all be used in this process. The use of palladium on carbon in the presence of atmospheric oxygen in a solvent such as toluene at 20°–115° C. is a particularly useful method to perform the transformation. The reaction is usually complete in 2 to 36 h.

Scheme 7

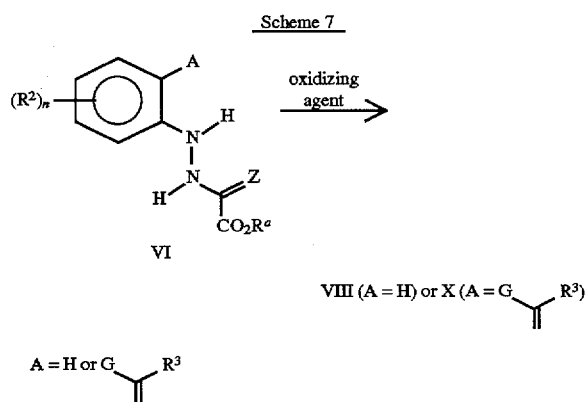

A = H or G $\underset{\|}{\overset{R^3}{\diagdown}}$

G = A and E taken together.
$R^a$ = alkyl

Compounds of Formula VI (Z=O) can be prepared by the treatment of hydrazines of Formula XI with oxalate esters of Formula XII as shown in Scheme 8. Hydrazines of Formula XI (where A=H) are commercially available. Although a variety of solvents can be used for the process, it is preferable to react an excess of the oxalate of Formula XII with the hydrazine of Formula XI in an alcoholic solvent. It is also desirable to utilize the same alcohol in both the solvent and the oxalate such that when diethyl oxalate is used as reagent, ethanol should be used as solvent. The reaction is generally carried out at room temperature using between 1.5 to 4 equivalents of the oxalate of Formula XII. The reaction is usually complete in 18 to 48 h.

Hydrazides of Formula VI (Z=S or $NR^{17}$) can be made as shown in Scheme 9. Thiooxalate esters of Formula XVII are known in the literature (Sawluk et al., *Synthesis*, 968–970 (1986)) and can be reacted with hydrazines of Formula XI under the conditions described for Scheme 8 to give compounds of Formula VI (Z=S) which in turn can be converted to compounds of Formula VI (Z=$NR^{17}$) by reaction with amines of Formula XVIII. The reaction of compounds of Formula VI (Z=S) with amines of Formula XVIII is best carried out by reaction in lower alcohols at temperatures from 0°–100° C.

Scheme 8

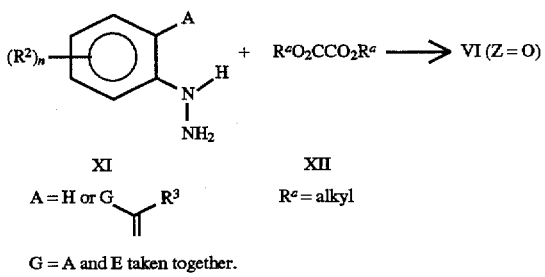

A = H or G $\underset{\|}{\overset{R^3}{\diagdown}}$ $R^a$ = alkyl

G = A and E taken together.

Compounds of Formula XI can be prepared as described in WO 91/17983. As shown in Scheme 10, Formula XI compounds (where A and E are taken together to form a ring) can be prepared from substituted anilines of Formula XIII by a diazotization/reduction sequence that is known in the literature (Enders, *Methoden Der Organischen Chemie*, E. Muller ed., George Thieme Verlag, Stuttgart, (1967), Volume X/2, pp 180–222). Compounds of Formula XIII are known in the art or can be obtained by methods analogous to known procedures. Those skilled in the art will recognize Formula XIII compounds as anilines.

Scheme 10

G = A and E taken together.

-continued
Scheme 10

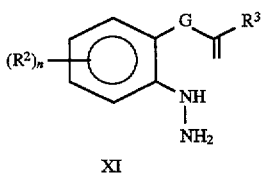

When reagents and reaction conditions for preparing compounds of Formula I are not compatible with functionalities present in the intermediates, the incorporation of protection/deprotection sequences into the synthesis will aid in obtaining the desired products. The use and choice of the protecting group will be apparent to one skilled in chemical synthesis.

EXAMPLE 1

4-(3-Chlorophenyl)-5,6-dihydro-5-phenyl-N-[4-(trifluoromethoxy)phenyl]-4H-1,3,4-oxadiazine-2-carboxamide Step A: Ethyl ethandioate-2-(3-chlorophenyl)hydrazide The compound, 3-chlorophenylhydrazine hydrochloride (60 g, 0.33 mol), was suspended in aqueous sodium hydroxide (1N, 500 mL) and extracted with diethyl ether. The ether extract was dried over magnesium sulfate and evaporated to yield the free hydrazine. The residue was dissolved in ethanol (100 mL) and treated with diethyl oxalate (100 mL, 0.48 mol) and stirred for 24 h at 25° C. The mixture was filtered and washed with diethyl ether to give the desired product (54 g) as a whim solid: m.p: 134°–135° C.

Step B: Ethyl 4-(3-Chlorophenyl)-5,6-dihydro-5-phenyl-4H-1,3,4-oxadiazine-2-carboxylate The product of Step A (10.3 g, 0.04 mol) was dissolved in DMF (100 mL) and treated with potassium carbonate (30 g, 0.22 mol). The temperature was raised to 100° C. and 1,2-(dibromoethyl)benzene (24.6 g, 0.09 mol in 60 mL of DMF) was added over 45 min. After 2 h of heating, 1,2-(dibromoethyl)benzene (8 g, 0.03 mol) and potassium carbonate (10 g, 0.07 mol) were added. After an additional 1 h of heating, second aliquots of 1,2-(dibromoethyl)benzene (8 g, 0.03 mol) and potassium carbonate (10 g, 0.07 mol) were added. After 2 additional h at 100° C., the mixture was cooled. The cooled mixture was added to water (500 mL), extracted with hexanes, and then extracted with ether. The combined organics were dried with magnesium sulfate and evaporated under reduced pressure. The residue was evaporated further at 80° C. under reduced pressure to remove DMF and other volatile contaminants. The red residue was subjected to silica gel chromatography with hexanes/ethyl acetate (5: 1). The first major product to elute was the 6-phenyl isomer. The later eluting 5-phenyl product was treated with methanol and evaporated to a yellow solid (1.5 g): m.p.: 103°–104° C.; NMR (CDCl$_3$) a 7.4–7.1 (m,7H), 7.0 (m, 1H), 6.9 (m, 1H), 5.2 (m, 1H), 4.6 (m, 1H), 4.4 (m,3H), 1.4 (m,3H).

Step C: 4-(3-Chlorophenyl)-5,6-dihydro-5-phenyl-N-[4-(trifluoromethoxy) phenyl]-4H-1,3,4-oxadiazine-2-carboxamide The compound 4-trifluoromethoxyaniline (1.0 mL, 0.007 mol), was dissolved in dichloromethane (50 mL), cooled in an ice bath, and treated with trimethyl aluminum (2M in hexanes, 3.5 mL, 0.007 mol). This mixture was stirred for 20 min. The product of Step B (1.2 g, 0.0035 mol), dissolved in dichloromethane (30 mL), was added and the reaction allowed to stir for 18 h at 25° C. The mixture was treated with aqueous hydrochloric acid (1N 20 mL) and water (50 mL). The layers were separated and the dichloromethane was dried with magnesium sulfate. The residue obtained after evaporation of solvent was subjected to chromatography on silica gel with hexanes/ethyl acetate (5:1 to 3: 1) as eluent. The desired material was isolated as a white solid (0.45 g): m.p.: 180° C.; NMR (CDCl$_3$) δ8.6 (br, 1H), 7.9 (m,2H), 7.4–7.0 (m,7H), 6.9 (m,2H), 5.2 (m, 1H), 4.7 (m, 1H), 4.5 (m, 1H).

By the procedures described herein the following compounds of Tables 1 and 2 can be prepared. The compounds in Table 1, line 1 can be referred to as 1-1, 1-2, 1-3 and 1-4 (as designated by line and column). All the other specific compounds covered in these Tables can be designated in an analogous fashion. The following abbreviations have been used in Tables 1 and 2: Me=methyl, i-Pr=isopropyl and Ph=phenyl.

TABLE 1

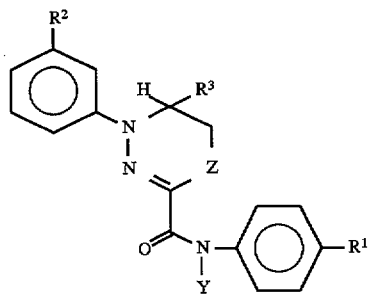

| | | COLUMN | | |
|---|---|---|---|---|
| | 1 | 2 | 3 | 4 |
| 1 Y = H; Z = O; R$^1$ = CF$_3$; R$^2$ = H; | R$^3$ = Ph | 4-F—Ph | 4-Cl—Ph | 4-CN—Ph |
| 2 Y = H; Z = O; R$^1$ = CF$_3$; R$^2$ = F; | R$^3$ = Ph | 4-F—Ph | 4-Cl—Ph | 4-CN—Ph |
| 3 Y = H; Z = O; R$^1$ = CF$_3$; R$^2$ = Cl; | R$^3$ = Ph | 4-F—Ph | 4-Cl—Ph | 4-CN—Ph |
| 4 Y = H; Z = O; R$^1$ = CF$_3$; R$^2$ = Br; | R$^3$ = Ph | 4-F—Ph | 4-Cl—Ph | 4-CN—Ph |
| 5 Y = H; Z = O; R$^1$ = CF$_3$; R$^2$ = CF$_3$; | R$^3$ = Ph | 4-F—Ph | 4-Cl—Ph | 4-CN—Ph |

TABLE 1-continued

| | | | COLUMN | | | |
|---|---|---|---|---|---|---|
| | | | 1 | 2 | 3 | 4 |
| 6 | Y = H; Z = O; R¹ = OCF₃; R² = H; | R³ = | Ph | 4-F—Ph | 4-Cl—Ph | 4-CN—Ph |
| 7 | Y = H; Z = O; R¹ = OCF₃; R² = F; | R³ = | Ph | 4-F—Ph | 4-Cl—Ph | 4-CN—Ph |
| 8 | Y = H; Z = O; R¹ = OCF₃; R² = Cl; | R³ = | Ph | 4-F—Ph | 4-Cl—Ph | 4-CN—Ph |
| 9 | Y = H; Z = O; R¹ = OCF₃; R² = Br; | R³ = | Ph | 4-F—Ph | 4-Cl—Ph | 4-CN—Ph |
| 10 | Y = H; Z = O; R¹ = OCF₃; R² = CF₃; | R³ = | Ph | 4-F—Ph | 4-Cl—Ph | 4-CN—Ph |
| 11 | Y = CO₂Me; Z = O; R¹ = CF₃; R² = H; | R³ = | Ph | 4-F—Ph | 4-Cl—Ph | 4-CN—Ph |
| 12 | Y = CO₂Me; Z = O; R¹ = CF₃; R² = F; | R³ = | Ph | 4-F—Ph | 4-Cl—Ph | 4-CN—Ph |
| 13 | Y = CO₂Me; Z = O; R¹ = CF₃; R² = Cl; | R³ = | Ph | 4-F—Ph | 4-Cl—Ph | 4-CN—Ph |
| 14 | Y = CO₂Me; Z = O; R¹ = CF₃; R² = Br; | R³ = | Ph | 4-F—Ph | 4-Cl—Ph | 4-CN—Ph |
| 15 | Y = CO₂Me; Z = O; R¹ = CF₃; R² = CF₃; | R³ = | Ph | 4-F—Ph | 4-Cl—Ph | 4-CN—Ph |
| 16 | Y = CO₂Me; Z = O; R¹ = OCF₃; R² = H; | R³ = | Ph | 4-F—Ph | 4-Cl—Ph | 4-CN—Ph |
| 17 | Y = CO₂Me; Z = O; R¹ = OCF₃; R² = F; | R³ = | Ph | 4-F—Ph | 4-Cl—Ph | 4-CN—Ph |
| 18 | Y = CO₂Me; Z = O; R¹ = OCF₃; R² = Cl; | R³ = | Ph | 4-F—Ph | 4-Cl—Ph | 4-CN—Ph |
| 19 | Y = CO₂Me; Z = O; R¹ = OCF₃; R² = Br; | R³ = | Ph | 4-F—Ph | 4-Cl—Ph | 4-CN—Ph |
| 20 | Y = CO₂Me; Z = O; R¹ = OCF₃; R² = CF₃; | R³ = | Ph | 4-F—Ph | 4-Cl—Ph | 4-CN—Ph |
| 21 | Y = H; Z = S; R¹ = CF₃; R² = H; | R³ = | Ph | 4-F—Ph | 4-Cl—Ph | 4-CN—Ph |
| 22 | Y = H; Z = S; R¹ = CF₃; R² = F; | R³ = | Ph | 4-F—Ph | 4-Cl—Ph | 4-CN—Ph |
| 23 | Y = H; Z = S; R¹ = CF₃; R² = Cl; | R³ = | Ph | 4-F—Ph | 4-Cl—Ph | 4-CN—Ph |
| 24 | Y = H; Z = S; R¹ = CF₃; R² = Br; | R³ = | Ph | 4-F—Ph | 4-Cl—Ph | 4-CN—Ph |
| 25 | Y = H; Z = S; R¹ = CF₃; R² = CF₃; | R³ = | Ph | 4-F—Ph | 4-Cl—Ph | 4-CN—Ph |
| 26 | Y = H; Z = S; R¹ = OCF₃; R² = H; | R³ = | Ph | 4-F—Ph | 4-Cl—Ph | 4-CN—Ph |
| 27 | Y = H; Z = S; R¹ = OCF₃; R² = F; | R³ = | Ph | 4-F—Ph | 4-Cl—Ph | 4-CN—Ph |
| 28 | Y = H; Z = S; R¹ = OCF₃; R² = Cl; | R³ = | Ph | 4-F—Ph | 4-Cl—Ph | 4-CN—Ph |
| 29 | Y = H; Z = S; R¹ = OCF₃; R² = Br; | R³ = | Ph | 4-F—Ph | 4-Cl—Ph | 4-CN—Ph |
| 30 | Y = H; Z = S; R¹ = OCF₃; R² = CF₃; | R³ = | Ph | 4-F—Ph | 4-Cl—Ph | 4-CN—Ph |
| 31 | Y = CO₂Me; Z = S; R¹ = CF₃; R² = H; | R³ = | Ph | 4-F—Ph | 4-Cl—Ph | 4-CN—Ph |
| 32 | Y = CO₂Me; Z = S; R¹ = CF₃; R² = F; | R³ = | Ph | 4-F—Ph | 4-Cl—Ph | 4-CN—Ph |
| 33 | Y = CO₂Me; Z = S; R¹ = CF₃; R² = Cl; | R³ = | Ph | 4-F—Ph | 4-Cl—Ph | 4-CN—Ph |
| 34 | Y = CO₂Me; Z = S; R¹ = CF₃; R² = Br; | R³ = | Ph | 4-F—Ph | 4-Cl—Ph | 4-CN—Ph |
| 35 | Y = CO₂Me; Z = S; R¹ = CF₃; R² = CF₃; | R³ = | Ph | 4-F—Ph | 4-Cl—Ph | 4-CN—Ph |
| 36 | Y = CO₂Me; Z = S; R¹ = OCF₃; R² = H; | R³ = | Ph | 4-F—Ph | 4-Cl—Ph | 4-CN—Ph |
| 37 | Y = CO₂Me; Z = S; R¹ = OCF₃; R² = F; | R³ = | Ph | 4-F—Ph | 4-Cl—Ph | 4-CN—Ph |
| 38 | Y = CO₂Me; Z = S; R¹ = OCF₃; R² = Cl; | R³ = | Ph | 4-F—Ph | 4-Cl—Ph | 4-CN—Ph |
| 39 | Y = CO₂Me; Z = S; R¹ = OCF₃; R² = Br; | R³ = | Ph | 4-F—Ph | 4-Cl—Ph | 4-CN—Ph |
| 40 | Y = CO₂Me; Z = S; R¹ = OCF₃; R² = CF₃; | R³ = | Ph | 4-F—Ph | 4-Cl—Ph | 4-CN—Ph |
| 41 | Y = H; Z = NH; R¹ = CF₃; R² = H; | R³ = | Ph | 4-F—Ph | 4-Cl—Ph | 4-CN—Ph |
| 42 | Y = H; Z = NH; R¹ = CF₃; R² = F; | R³ = | Ph | 4-F—Ph | 4-Cl—Ph | 4-CN—Ph |
| 43 | Y = H; Z = NH; R¹ = OCF₃; R² = H; | R³ = | Ph | 4-F—Ph | 4-Cl—Ph | 4-CN—Ph |
| 44 | Y = H; Z = NH; R¹ = OCF₃; R² = F; | R³ = | Ph | 4-F—Ph | 4-Cl—Ph | 4-CN—Ph |
| 45 | Y = H; Z = NCH₃; R¹ = CF₃; R² = Cl; | R³ = | Ph | 4-F—Ph | 4-Cl—Ph | 4-CN—Ph |
| 46 | Y = H; Z = NCH₃; R¹ = CF₃; R² = Br; | R³ = | Ph | 4-F—Ph | 4-Cl—Ph | 4-CN—Ph |
| 47 | Y = H; Z = NCH₃; R¹ = CF₃; R² = CF₃; | R³ = | Ph | 4-F—Ph | 4-Cl—Ph | 4-CN—Ph |
| 48 | Y = H; Z = NCH₃; R¹ = OCF₃; R² = Cl; | R³ = | Ph | 4-F—Ph | 4-Cl—Ph | 4-CN—Ph |
| 49 | Y = H; Z = NCH₃; R¹ = OCF₃; R² = Br; | R³ = | Ph | 4-F—Ph | 4-Cl—Ph | 4-CN—Ph |
| 50 | Y = H; Z = NCH₃; R¹ = OCF₃; R² = CF₃; | R³ = | Ph | 4-F—Ph | 4-Cl—Ph | 4-CN—Ph |
| 51 | Y = H; Z = NCOCH₃; R¹ = CF₃; R² = Cl; | R³ = | Ph | 4-F—Ph | 4-Cl—Ph | 4-CN—Ph |
| 52 | Y = H; Z = NCOCH₃; R¹ = CF₃; R² = Br; | R³ = | Ph | 4-F—Ph | 4-Cl—Ph | 4-CN—Ph |
| 53 | Y = H; Z = NCOCH₃; R¹ = CF₃; R² = CF₃; | R³ = | Ph | 4-F—Ph | 4-Cl—Ph | 4-CN—Ph |
| 54 | Y = H; Z = NCOCH₃; R¹ = OCF₃; R² = Cl; | R³ = | Ph | 4-F—Ph | 4-Cl—Ph | 4-CN—Ph |
| 55 | Y = H; Z = NCOCH₃; R¹ = OCF₃; R² = Br; | R³ = | Ph | 4-F—Ph | 4-Cl—Ph | 4-CN—Ph |
| 56 | Y = H; Z = NCOCH₃; R¹ = OCF₃; R² = CF₃; | R³ = | Ph | 4-F—Ph | 4-Cl—Ph | 4-CN—Ph |
| 57 | Y = CO₂Me; Z = NH; R¹ = CF₃; R² = Cl; | R³ = | Ph | 4-F—Ph | 4-Cl—Ph | 4-CN—Ph |
| 58 | Y = CO₂Me; Z = NH; R¹ = CF₃; R² = Br; | R³ = | Ph | 4-F—Ph | 4-Cl—Ph | 4-CN—Ph |
| 59 | Y = CO₂Me; Z = NH; R¹ = CF₃; R² = CF₃; | R³ = | Ph | 4-F—Ph | 4-Cl—Ph | 4-CN—Ph |
| 60 | Y = CO₂Me; Z = NH; R¹ = OCF₃; R² = Cl; | R³ = | Ph | 4-F—Ph | 4-Cl—Ph | 4-CN—Ph |
| 61 | Y = CO₂Me; Z = NH; R¹ = OCF₃; R² = Br; | R³ = | Ph | 4-F—Ph | 4-Cl—Ph | 4-CN—Ph |
| 62 | Y = CO₂Me; Z = NH; R¹ = OCF₃; R² = CF₃; | R³ = | Ph | 4-F—Ph | 4-Cl—Ph | 4-CN—Ph |

TABLE 2

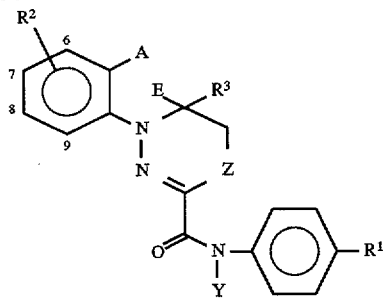

| | | COLUMN | | |
|---|---|---|---|---|
| | 1 | 2 | 3 | 4 |

| | | | | | |
|---|---|---|---|---|---|
| 63  A + E = CH$_2$; Z = O; Y = H; R$^1$ = CF$_3$; R$^2$ = 6-F; | R$^3$ = | i-Pr | Ph | CO$_2$Me | 4-F—Ph |
| 64  A + E = CH$_2$; Z = O; Y = H; R$^1$ = CF$_3$; R$^2$ = 6-Cl; | R$^3$ = | i-Pr | Ph | CO$_2$Me | 4-F—Ph |
| 65  A + E = CH$_2$; Z = O; Y = H; R$^1$ = CF$_3$; R$^2$ = 7-F; | R$^3$ = | i-Pr | Ph | CO$_2$Me | 4-F—Ph |
| 66  A + E = CH$_2$; Z = O; Y = H; R$^1$ = CF$_3$; R$^2$ = 7-Cl; | R$^3$ = | i-Pr | Ph | CO$_2$Me | 4-F—Ph |
| 67  A + E = CH$_2$; Z = O; Y = H; R$^1$ = CF$_3$; R$^2$ = 7-CF$_3$; | R$^3$ = | i-Pr | Ph | CO$_2$Me | 4-F—Ph |
| 68  A + E = CH$_2$; Z = O; Y = H; R$^1$ = OCF$_3$; R$^2$ = 6-F; | R$^3$ = | i-Pr | Ph | CO$_2$Me | 4-F—Ph |
| 69  A + E = CH$_2$; Z = O; Y = H; R$^1$ = OCF$_3$; R$^2$ = 6-Cl; | R$^3$ = | i-Pr | Ph | CO$_2$Me | 4-F—Ph |
| 70  A + E = CH$_2$; Z = O; Y = H; R$^1$ = OCF$_3$; R$^2$ = 7-F; | R$^3$ = | i-Pr | Ph | CO$_2$Me | 4-F—Ph |
| 71  A + E = CH$_2$; Z = O; Y = H; R$^1$ = OCF$_3$; R$^2$ = 7-Cl; | R$^3$ = | i-Pr | Ph | CO$_2$Me | 4-F—Ph |
| 72  A + E = CH$_2$; Z = O; Y = H; R$^1$ = OCF$_3$; R$^2$ = 7-CF$_3$; | R$^3$ = | i-Pr | Ph | CO$_2$Me | 4-F—Ph |
| 73  A + E = OCH$_2$; Z = O; Y = H; R$^1$ = CF$_3$; R$^2$ = 6-F; | R$^3$ = | i-Pr | Ph | CO$_2$Me | 4-F—Ph |
| 74  A + E = OCH$_2$; Z = O; Y = H; R$^1$ = OCF$_3$; R$^2$ = 6-F; | R$^3$ = | i-Pr | Ph | CO$_2$Me | 4-F—Ph |
| 75  A + E = OCH$_2$; Z = O; Y = H; R$^1$ = CF$_3$; R$^2$ = 6-Cl; | R$^3$ = | i-Pr | Ph | CO$_2$Me | 4-F—Ph |
| 76  A + E = OCH$_2$; Z = O; Y = H; R$^1$ = OCF$_3$; R$^2$ = 6-Cl; | R$^3$ = | i-Pr | Ph | CO$_2$Me | 4-F—Ph |
| 77  A + E = CH$_2$; Z = O; Y = CO$_2$Me; R$^1$ = CF$_3$; R$^2$ = 6-F; | R$^3$ = | i-Pr | Ph | CO$_2$Me | 4-F—Ph |
| 78  A + E = CH$_2$; Z = O; Y = CO$_2$Me; R$^1$ = OCF$_3$; R$^2$ = 6-F; | R$^3$ = | i-Pr | Ph | CO$_2$Me | 4-F—Ph |
| 79  A + E = CH$_2$; Z = O; Y = CO$_2$Me; R$^1$ = CF$_3$; R$^2$ = 6-Cl; | R$^3$ = | i-Pr | Ph | CO$_2$Me | 4-F—Ph |
| 80  A + E = CH$_2$; Z = O; Y = CO$_2$Me; R$^1$ = OCF$_3$; R$^2$ = 6-Cl; | R$^3$ = | i-Pr | Ph | CO$_2$Me | 4-F—Ph |
| 81  A + E = CH$_2$; Z = S; Y = H; R$^1$ = CF$_3$; R$^2$ = 6-F; | R$^3$ = | i-Pr | Ph | CO$_2$Me | 4-F—Ph |
| 82  A + E = CH$_2$; Z = S; Y = H; R$^1$ = CF$_3$; R$^2$ = 6-Cl; | R$^3$ = | i-Pr | Ph | CO$_2$Me | 4-F—Ph |
| 83  A + E = CH$_2$; Z = S; Y = H; R$^1$ = OCF$_3$; R$^2$ = 6-F; | R$^3$ = | i-Pr | Ph | CO$_2$Me | 4-F—Ph |
| 84  A + E = CH$_2$; Z = S; Y = H; R$^1$ = OCF$_3$; R$^2$ = 6-Cl; | R$^3$ = | i-Pr | Ph | CO$_2$Me | 4-F—Ph |
| 85  A + E = CH$_2$; Z = S; Y = H; R$^1$ = CF$_3$; R$^2$ = 7-F; | R$^3$ = | i-Pr | Ph | CO$_2$Me | 4-F—Ph |
| 86  A + E = CH$_2$; Z = S; Y = H; R$^1$ = CF$_3$; R$^2$ = 7-Cl; | R$^3$ = | i-Pr | Ph | CO$_2$Me | 4-F—Ph |
| 87  A + E = CH$_2$; Z = S; Y = H; R$^1$ = CF$_3$; R$^2$ = 7-CF$_3$; | R$^3$ = | i-Pr | Ph | CO$_2$Me | 4-F—Ph |
| 88  A + E = CH$_2$; Z = S; Y = H; R$^1$ = OCF$_3$; R$^2$ = 7-F; | R$^3$ = | i-Pr | Ph | CO$_2$Me | 4-F—Ph |
| 89  A + E = CH$_2$; Z = S; Y = H; R$^1$ = OCF$_3$; R$^2$ = 7-Cl; | R$^3$ = | i-Pr | Ph | CO$_2$Me | 4-F—Ph |
| 90  A + E = CH$_2$; Z = S; Y = H; R$^1$ = OCF$_3$; R$^2$ = 7-CF$_3$; | R$^3$ = | i-Pr | Ph | CO$_2$Me | 4-F—Ph |
| 91  A + E = OCH$_2$; Z = S; Y = H; R$^1$ = CF$_3$; R$^2$ = 6-F; | R$^3$ = | i-Pr | Ph | CO$_2$Me | 4-F—Ph |
| 92  A + E = OCH$_2$; Z = S; Y = H; R$^1$ = OCF$_3$; R$^2$ = 6-F; | R$^3$ = | i-Pr | Ph | CO$_2$Me | 4-F—Ph |
| 93  A + E = OCH$_2$; Z = S; Y = H; R$^1$ = CF$_3$; R$^2$ = 6-Cl; | R$^3$ = | i-Pr | Ph | CO$_2$Me | 4-F—Ph |
| 94  A + E = OCH$_2$; Z = S; Y = H; R$^1$ = OCF$_3$; R$^2$ = 6-Cl; | R$^3$ = | i-Pr | Ph | CO$_2$Me | 4-F—Ph |
| 95  A + E = CH$_2$; Z = S; Y = CO$_2$Me; R$^1$ = CF$_3$; R$^2$ = 6-F; | R$^3$ = | i-Pr | Ph | CO$_2$Me | 4-F—Ph |
| 96  A + E = CH$_2$; Z = S; Y = CO$_2$Me; R$^1$ = OCF$_3$; R$^2$ = 6-F; | R$^3$ = | i-Pr | Ph | CO$_2$Me | 4-F—Ph |
| 97  A + E = CH$_2$; Z = S; Y = CO$_2$Me; R$^1$ = CF$_3$; R$^2$ = 6-Cl; | R$^3$ = | i-Pr | Ph | CO$_2$Me | 4-F—Ph |
| 98  A + E = CH$_2$; Z = S; Y = CO$_2$Me; R$^1$ = OCF$_3$; R$^2$ = 6-Cl; | R$^3$ = | i-Pr | Ph | CO$_2$Me | 4-F—Ph |
| 99  A + E = CH$_2$; Z = NH; Y = H; R$^1$ = CF$_3$; R$^2$ = 6-F; | R$^3$ = | i-Pr | Ph | CO$_2$Me | 4-F—Ph |
| 100  A + E = CH$_2$; Z = NH; Y = H; R$^1$ = CF$_3$; R$^2$ = 6-Cl; | R$^3$ = | i-Pr | Ph | CO$_2$Me | 4-F—Ph |
| 101  A + E = CH$_2$; Z = NMe; Y = H; R$^1$ = OCF$_3$; R$^2$ = 6-F; | R$^3$ = | i-Pr | Ph | CO$_2$Me | 4-F—Ph |
| 102  A + E = CH$_2$; Z = NMe; Y = H; R$^1$ = OCF$_3$; R$^2$ = 6-Cl; | R$^3$ = | i-Pr | Ph | CO$_2$Me | 4-F—Ph |
| 103  A + E = CH$_2$; Z = NCOMe; Y = H; R$^1$ = CF$_3$; R$^2$ = 7-F; | R$^3$ = | i-Pr | Ph | CO$_2$Me | 4-F—Ph |
| 104  A + E = CH$_2$; Z = NCOMe; Y = H; R$^1$ = CF$_3$; R$^2$ = 7-Cl; | R$^3$ = | i-Pr | Ph | CO$_2$Me | 4-F—Ph |
| 105  A + E = CH$_2$; Z = NCOMe; Y = H; R$^1$ = CF$_3$; R$^2$ = 7-CF$_3$; | R$^3$ = | i-Pr | Ph | CO$_2$Me | 4-F—Ph |
| 106  A + E = CH$_2$; Z = NCOMe; Y = H; R$^1$ = OCF$_3$; R$^2$ = 7-F; | R$^3$ = | i-Pr | Ph | CO$_2$Me | 4-F—Ph |
| 107  A + E = CH$_2$; Z = NCOMe; Y = H; R$^1$ = OCF$_3$; R$^2$ = 7-Cl; | R$^3$ = | i-Pr | Ph | CO$_2$Me | 4-F—Ph |
| 108  A + E = CH$_2$; Z = NCOMe; Y = H; R$^1$ = OCF$_3$; R$^2$ = 7-CF$_3$; | R$^3$ = | i-Pr | Ph | CO$_2$Me | 4-F—Ph |
| 109  A + E = CH$_2$; Z = NCO$_2$Me; Y = H; R$^1$ = CF$_3$; R$^2$ = 7-F; | R$^3$ = | i-Pr | Ph | CO$_2$Me | 4-F—Ph |
| 110  A + E = CH$_2$; Z = NCO$_2$Me; Y = H; R$^1$ = CF$_3$; R$^2$ = 7-Cl; | R$^3$ = | i-Pr | Ph | CO$_2$Me | 4-F—Ph |
| 111  A + E = CH$_2$; Z = NCO$_2$Me; Y = H; R$^1$ = CF$_3$; R$^2$ = 7-CF$_3$; | R$^3$ = | i-Pr | Ph | CO$_2$Me | 4-F—Ph |
| 112  A + E = CH$_2$; Z = NCO$_2$Me; Y = H; R$^1$ = OCF$_3$; R$^2$ = 7-F; | R$^3$ = | i-Pr | Ph | CO$_2$Me | 4-F—Ph |
| 113  A + E = CH$_2$; Z = NCO$_2$Me; Y = H; R$^1$ = OCF$_3$; R$^2$ = 7-Cl; | R$^3$ = | i-Pr | Ph | CO$_2$Me | 4-F—Ph |
| 114  A + E = CH$_2$; Z = NCO$_2$Me; Y = H; R$^1$ = OCF$_3$; R$^2$ = 7-CF$_3$; | R$^3$ = | i-Pr | Ph | CO$_2$Me | 4-F—Ph |
| 115  A + E = OCH$_2$; Z = NH; Y = H; R$^1$ = CF$_3$; R$^2$ = 6-F; | R$^3$ = | i-Pr | Ph | CO$_2$Me | 4-F—Ph |
| 116  A + E = OCH$_2$; Z = NH; Y = H; R$^1$ = OCF$_3$; R$^2$ = 6-F; | R$^3$ = | i-Pr | Ph | CO$_2$Me | 4-F—Ph |
| 117  A + E = OCH$_2$; Z = NH; Y = H; R$^1$ = CF$_3$; R$^2$ = 6-Cl; | R$^3$ = | i-Pr | Ph | CO$_2$Me | 4-F—Ph |
| 118  A + E = OCH$_2$; Z = NH; Y = H; R$^1$ = OCF$_3$; R$^2$ = 6-Cl; | R$^3$ = | i-Pr | Ph | CO$_2$Me | 4-F—Ph |
| 119  A + E = CH$_2$; Z = NH; Y = CO$_2$Me; R$^1$ = CF$_3$; R$^2$ = 6-F; | R$^3$ = | i-Pr | Ph | CO$_2$Me | 4-F—Ph |
| 120  A + E = CH$_2$; Z = NH; Y = CO$_2$Me; R$^1$ = OCF$_3$; R$^2$ = 6-F; | R$^3$ = | i-Pr | Ph | CO$_2$Me | 4-F—Ph |
| 121  A + E = CH$_2$; Z = NH; Y = CO$_2$Me; R$^1$ = CF$_3$; R$^2$ = 6-Cl; | R$^3$ = | i-Pr | Ph | CO$_2$Me | 4-F—Ph |

TABLE 2-continued

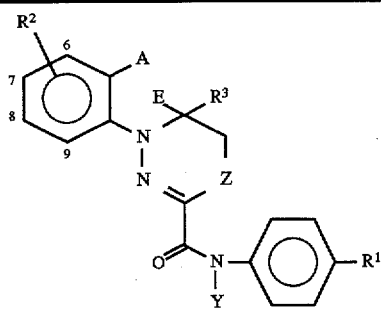

| | COLUMN | | | |
|---|---|---|---|---|
| | 1 | 2 | 3 | 4 |
| 122 A + E = CH$_2$; Z = NH; Y = CO$_2$Me; R$^1$ = OCF$_3$; R$^2$ = 6-Cl; R$^3$ = | i-Pr | Ph | CO$_2$Me | 4-F—Ph |

Formulation/Utility

Compounds of this invention will generally be used in formulation with an agriculturally suitable carrier comprising a liquid or solid diluent. Useful formulations include dusts, granules, baits, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 5–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., Handbook of Insecticide Dust Diluents and Carriers, 2nd Ed., Dorland Books, Caldwell, N.J. Typical liquid diluents and solvents are described in Marsden, Solvents Guide, 2nd Ed., Interscience, New York, 1950. McCutcheon's Detergents and Emulsifiers Annual, Allured Publ. Corp., Ridgewood, N.J., as well as Sisely and Wood, Encyclopedia of Surface Active Agents, Chemical Publ. Co., Inc., New York, 1964, list surfactants and recommended uses. All formulations can contain minor amounts of additives to reduce foam, caking, corrosion, microbiological growth, and the like.

Solutions are prepared by simply mixing the ingredients. Fine solid compositions are made by blending and, usually, grinding as in a hammer mill or fluid energy mill. Water-dispersible granules can be produced by agglomerating a free powder composition; see for example, Cross et al., Pesticide Formulations, Washington, D. C., (1988), pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", Chemical Engineering, December 4, (1967), pp 147–148, Perry's Chemical Engineer's Handbook, 4th Ed., McGraw-Hill, New York, (1963), pp 8–57 and following, and WO 91/13546.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, Weed Control as a Science, John Wiley and Sons, New York, (1961), pp 81–96; and Hance et al., Weed Control Handbook, 8th Ed., Blackwell Scientific Publications, Oxford, (1989).

In the following Examples, all percentages are by weight and all formulations are prepared in conventional ways. Compound numbers refer to compounds in Index Table A.

| Example A | |
|---|---|
| Wettable Powder | |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |
| Example B | |
| Granule | |
| Compound 1 | 10.0% |
| attapulgite granules (low volatile matter, 0.71/0.30 mm; U.S.S. No. 25–50 sieves) | 90.0%. |
| Example C | |
| Extruded Pellet | |
| Compound 1 | 25.0% |
| anhydrous sodium sulfate | 10.0% |
| crude calcium ligninsulfonate | 5.0% |
| sodium alkylnaphthalenesulfonate | 1.0% |

-continued

| calcium/magnesium bentonite | 59.0%. |

Example D

Emulsifiable Concentrate

| Compound 1 | 20.0% |
| blend of oil soluble sulfonates and polyoxyethylene ethers | 10.0% |
| isophorone | 70.0%. |

The compounds of this invention exhibit activity against a wide spectrum of foliar-feeding, fruit-feeding, stem- or root-feeding, seed-feeding, aquatic and soft-inhabiting arthropods (term "arthropods" includes insects, mites and nematodes) which are pests of growing and stored agronomic crops, forestry, greenhouse crops, ornamentals, nursery crops, stored food and fiber products, livestock, household, and public and animal health. Those skilled in the art will appreciate that not all compounds are equally effective against all growth stages of all pests. Nevertheless, all of the compounds of this invention display activity against pests that include: eggs, larvae and adults of the Order Lepidoptera; eggs, foliar-feeding, fruit-feeding, root-feeding, seed-feeding larvae and adults of the Order Coleoptera; eggs, immatures and adults of the Orders Hemiptera and Homoptera; eggs, larvae, nymphs and adults of the Order Acari; eggs, immatures and adults of the Orders Thysanoptera, Orthoptera and Dermaptera; eggs, immatures and adults of the Order Diptera; and eggs, junveniles and adults of the Phylum Nematoda. The compounds of this invention are also active against pests of the Orders Hymenoptera, Isoptera, Siphonaptera, Blattaria, Thysanura and Psocoptera; pests belonging to the Class Arachnida and Phylum Platyhelminthes. Specifically, the compounds are active against southern corn rootworm (*Diabrotica undecimpunctata howardi*), aster leafhopper (*Mascrosteles fascifrons*), boll weevil (*Anthonomus grandis*), two-spotted spider mite (*Tetranychus urticae*), fall armyworm (*Spodoptera frugiperda*), black bean aphid (*Aphis fabae*), green peach aphid (*Myzus persica*), cotton aphid (*Aphis gossypii*), Russian wheat aphid (*Diuraphis noxia*), English grain aphid (*Sitobion avenae*), tobacco budworm (*Heliothis virescens*), rice water weevil (*Lissorhoptrus oryzophilus*), rice leaf beetle (*Oulema oryzae*), whitebacked planthopper (*Sogatella furcifera*), green leafhopper (*Nephotettix cincticeps*), brown planthopper (*Nilaparvata lugens*), small brown planthopper (*Laodelphax striatellus*), rice stem borer (*Chilo suppressalis*), rice leafroller (*Cnaphalocrocis medinalis*), black rice stink bug (*Scotinophara lurida*), rice stink bug (*Oebalus pugnax*), rice bug (*Leptocorisa chinensis*), slender rice bug (*Cletus puntiger*), and southern green stink bug (*Nezara viridula*). The compounds are active on mites, demonstrating ovicidal, larvicidal and chemosterilant activity against such families as Tetranychidae including *Tetranychus urticae*, *Tetranychus cinnabarinus*, *Tetranychus mcdanieli*, *Tetranychus pacificus*, *Tetranychus turkestani*, *Byrobia rubrioculus*, *Panonychus ulmi*, *Panonychus citri*, *Eotetranychus carpini borealis*, *Eotetranychus*, *hicoriae*, *Eotetranychus sexmaculatus*, *Eotetranychus yumensis*, *Eotetranychus banksi* and *Oligonychus pratensis*; Tenuipalpidae including *Brevipalpus lewisi*, *Brevipalpus phoenicis*, *Brevipalpus californicus* and *Brevipalpus obovatus*; Eriophyidae including *Phyllocoptruta oleivora*, *Eriophyes sheldoni*, *Aculus cornutus*, *Epitrimerus pyri* and *Eriophyes mangiferae*. See WO 90/10623 and WO 92/00673 for more detailed pest descriptions.

Compounds of this invention can also be mixed with one or more other insecticides, fungicides, nematocides, bactericides, acaricides, growth regulators, chemosterilants, semiochemicals, repellants, attractants, pheromones, feeding stimulants or other biologically active compounds to form a multi-component pesticide giving an even broader spectrum of agricultural protection. Examples of other agricultural protectants with which compounds of this invention can be formulated are: insecticides such as avermectin B, monocrotophos, carbofuran, tetrachlorvinphos, malathion, parathion-methyl, methomyl, chlordimeform, diazinon, deltamethrin, oxamyl, fenvalerate, esfenvalerate, permethrin, profenofos, sulprofos, triflumuron, diflubenzuron, methoprene, buprofezin, thiodicarb, acephate, azinphosmethyl, chlorpyrifos, dimethoate, fipronil, flufenprox, fonophos, isofenphos, methidathion, metha-midophos, phosmet, phosphamidon, phosalone, pirimicarb, phorate, terbufos, trichlorfon, methoxychlor, bifenthrin, biphenate, cyfluthrin, tefluthrin, fenpropathrin, fluvalinate, flucythrinate, tralomethrin, imidacloprid, metaldehyde and rotenone; fungicides such as carbendazim, thiuram, dodine, maneb, chloroneb, benomyl, cymoxanil, fenpropidine, fenpropimorph, triadimefon, captan, thiophanate-methyl, thiabendazole, phosethyl-Al, chlorothalonil, dichloran, metalaxyl, captafol, iprodione, oxadixyl, vinclozolin, kasugamycin, myclobutanil, tebuconazole, difenoconazole, diniconazole, fluquinconazole, ipconazole, metconazole, penconazole, propiconazole, uniconzole, flutriafol, prochloraz, pyrifenox, fenarimol, triadimenol, diclobutrazol, copper oxychloride, furalaxyl, folpet, flusilazol, blasticidin S, diclomezine, edifenphos, isoprothiolane, iprobenfos, mepronil, neo-asozin, pencycuron, probenazole, pyroquilon, tricyclazole, validamycin, and flutolanil; nematocides such as aldoxycarb, fenamiphos and fosthietan; bactericides such as oxytetracyline, streptomycin and tribasic copper sulfate; acaricides such as binapacryl, oxythioquinox, chlorobenzilate, dicofol, dienochlor, cyhexatin, hexythiazox, amitraz, propargite, tebufenpyrad and fenbutatin oxide; and biological agents such as entomopathogenic bacteria, virus and fungi.

In certain instances, combinations with other arthropodicides having a similiar spectrum of control but a different mode of action will be particularly advantageous for resistance management.

Arthropod pests are controlled and protection of agronomic, horticultural and specialty crops, animal and human health is achieved by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of foliar and soil inhabiting arthropods and nematode pests and protection of agronomic and/or nonagronomic crops, comprising applying one or more of the compounds of Formula I, or compositions containing at least one such compound, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, seed coats, microencapsulations, systemic uptake, baits, eartags, boluses, foggers, fumigants, aerosols, dusts and many others. The compounds can be incorporated into baits that are consumed by the arthropods or in devices such as traps and the like.

The compounds of this invention can be applied in their pure state, but most often application will be of a formulation comprising one or more compounds with suitable carriers (diluents and surfactants) and possibly in combination with a food depending on the contemplated end use. A preferred method of application involves spraying a water dispersion or refined oil solution of the compounds. Combinations with spray oils, spray oil concentrations, spreader stickers, adjuvants, and synergists and other solvents such as piperonyl butoxide often enhance compound efficacy.

The rate of application required for effective control will depend on such factors as the species of arthropod to be controlled, the pest's life cycle, life stage, size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.001 kg/hectare may be sufficient or as much as 8 kg hectare may be required. For nonagronomic applications, effective use rates will range from about 1.0 to 50 mg/square meter but as little as 0.1 mg/square meter may be sufficient or as much as 150 mg/square meter may be required.

The following TESTS demonstrate the control efficacy of compounds of this invention on specific pests. "Control efficacy" represents inhibition of arthropod development (including mortality) that causes significantly reduced feeding. The pest control protection afforded by the compounds is not limited, however, to these species. See Index Table A for compound descriptions.

Index Table A

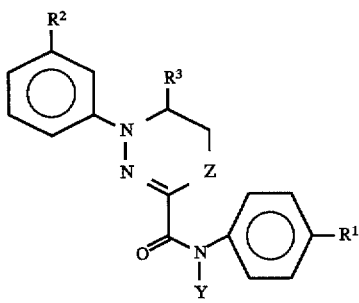

| CMPD | R$^1$ | R$^2$ | Y | Z | R$^3$ | m.p. (°C.) |
|---|---|---|---|---|---|---|
| 1 | OCF$_3$ | Cl | H | O | Me | oil$^a$ |
| 2 | OCF$_3$ | Cl | H | O | Et | oil$^b$ |
| 3 | OCF$_3$ | Cl | H | O | i-Pr | foam$^c$ |
| 4 | OCF$_3$ | Cl | H | O | Ph | 180 |
| 5 | OCF$_3$ | H | H | O | Ph | 180 |
| 6 | OCF$_3$ | H | H | O | Me | oil$^d$ |
| 7 | OCF$_3$ | CF$_3$ | H | O | Ph | 142–143 |
| 8 | OCF$_3$ | CF$_3$ | CO$_2$Me | O | Ph | 119–120 |
| 9 | OCF$_3$ | CF$_3$ | H | O | 4-F-Ph | 75–80 |
| 10 | OCF$_3$ | Cl | H | O | 4-F-Ph | 75–80 |
| 11 | OCF$_3$ | CF$_3$ | H | O | i-Pr | oil$^e$ |
| 12 | OCF$_3$ | CF$_3$ | Me | O | Ph | 160–161 |
| 13 | OCF$_3$ | CF$_3$ | H | O | Me | 86–90 |
| 14 | OCF$_3$ | CF$_3$ | H | O | Et | 106–108 |
| 15 | OCF$_3$ | CF$_3$ | CO$_2$Me | O | 4-F-Ph | oil$^f$ |
| 16 | OCF$_3$ | Cl | CO$_2$Me | O | 4-F-Ph | oil$^g$ |
| 17 | OCK$_3$ | Cl | Me | O | 4-F-Ph | 130–133 |
| 18 | OCF$_3$ | CF$_3$ | Me | O | 4-F-Ph | 142–144 |
| 19 | OCF$_3$ | F | H | O | 4-F-Ph | 191 |

NMR(CDCl$_3$)
$^a$δ 8.7(br s, 1H), 7.7(m, 2H), 7.3(m, 4H), 7.1(m, 1H), 6.9(m, 1H), 4.4(m, 1H), 4.3(m, 2H), 1.35(m, 3H).

-continued

Index Table A

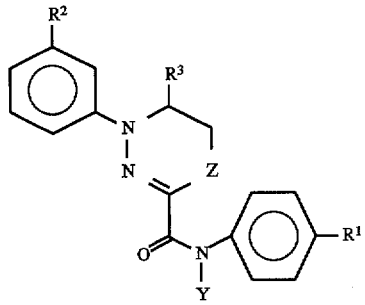

| CMPD | R$^1$ | R$^2$ | Y | Z | R$^3$ | m.p. (°C.) |
|---|---|---|---|---|---|---|

$^b$δ 8.7(br s, 1H), 7.7(m, 2H), 7.3(m, 4H), 7.1(m, 1H), 6.9(m, 1H), 4.6(m, 1H), 4.3(m, 1H), 4.0(m, 1H), 1.8(m, 2H), 1.1(m,3H).
$^c$δ 8.7(br s, 1H), 7.7(m, 2H), 7.3(m, 4H), 7.1(m, 1H), 6.9(m, 1H), 4.7(m, 1H), 4.7(m, 1H), 4.1(m, 1H), 3.95(m, 1H), 2.2(m, 1H), 1.0(m, 6H).
$^d$δ 8.6(br s, 1H), 7.7–7.0(m, 9H), 4.4(m, 3H), 1.4(m, 3H).
$^e$δ 8.7(br, 1H), 7.5–7.0(m, 8H), 4.8(m, 4H), 7.1(m, 1H), 4.2(m, 2H), 2.1(m, 1H), 1.6(m, 6H).
$^f$δ 7.4–7.0(m, 12H), 5.3(m, 1H), 4.6(m, 2H), 3.8(2, 3H).
$^g$δ 7.3–6.9(m, 12H), 5.2(m, 1H), 4.5(m, 2H), 3.8(s, 3H).

TEST A

Fall Armyworm

Test units, each consisting of a H.I.S. (high impact styrene) tray with 16 cells were prepared. Wet filter paper and approximately 8 cm$^2$ of lima bean leaf was placed into twelve of the cells. A 0.5 cm layer of wheat germ diet was placed into the four remaining cells. Fifteen to twenty third-instar larvae of fail armyworm (Spodoptera frugiperda) were placed into a 230 mL (8 ounce) plastic cup. Solutions of each of the test compounds in 75/25 acetone/ distilled water solvent were sprayed into the tray and cup. Spraying was accomplished by passing the tray and cup on a conveyer belt directly beneath a flat fan hydraulic nozzle which discharged the spray at a rate of 0.55 kg of active ingredient per hectare (about 0.5 pounds per acre) at 207 kPa (30 p.s.i.). The insects were transferred from the 230 mL cup to the H.I.S. tray (one insect per cell). The trays were covered and held at 27° C. and 50% relative humidity for 48 h, after which time readings were taken on the twelve cells with lima bean leaves. The 4 four remaining cells were read at 6–8 days for delayed toxicity. Of the compounds tested, the following gave control efficacy levels of 80% or greater: 1, 2, 3, 4, 5, 7, 8, 9, 10, 11, 12, 13, 14, 15, 16, 17, 18 and 19.

TEST B

Tobacco Budworm

The test procedure of TEST A was repeated to determine efficacy against third-instar larvae of the tobacco budworm (Heliothis virescens) except that three 230 mL (8 ounce) plastic cups with wheat germ diet were used in place of the H.I.S. tray, with each cup pre-infested with 5 third-instar larvae. Of the compounds tested, the following gave mortality levels of 80% or higher: 3, 7, 8, 9, 10, 12, 14, 15, 16 and 18.

TEST C

Southern Corn Rootworm

Test units, each consisting of a 230 mL (8 ounce) plastic cup containing a 2.54 cm$^2$ plug (1 square inch) of a wheatgerm diet, were prepared. The test units were sprayed as described in TEST A with individual solutions of the test compounds. After the spray on the cups had dried, five second-instar larvae of the southern corn rootworm (*Diabrotica undecimpunctata howardi*) were placed into each cup. The cups were held at 27° C. and 50% relative humidity for 48 h, after which time mortality readings were taken. The same units were read again at 6–8 days for delayed toxicity. Of the compounds tested, the following gave control efficacy levels of 80% or greater: 1, 2, 4, 5, 6, 9, 10, 12, 13, 14 and 19.

TEST D

Boll Weevil

Test units consisting of 260 mL (9 ounce) cups containing five adult boll weevils (*Anthonomus grandis grandis*) were prepared. The test units were sprayed as described in TEST A with individual solutions of the test compounds. Each cup was covered with a vented lid and held at 27° C. and 50% relative humidity for 48 h, after which time mortality readings were taken. Of the compounds tested, the following gave mortality levels of 80% or higher: 3, 4, 7, 9, 10, 18 and 19.

I claim:
1. A compound of the formula

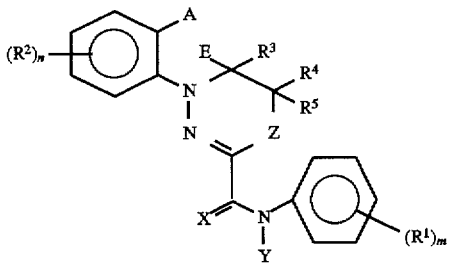

wherein:

A is H;

E is selected from the group H and $C_1$–$C_3$ alkyl; or

A and E are taken together to form a member selected from the group $CH_2$, $CH_2CH_2$, O, $S(O)_r$, $NR^6$, $OCH_2$, $S(O)_rCH_2$, $N(R^6)CH_2$, substituted $CH_2$, and substituted $CH_2CH_2$, the substituents independently selected from 1–2 halogen and 1–2 methyl;

X and $X^1$ are independently selected from the group O and S;

Y is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_3$–$C_6$ cycloalkyl, $C_3$–$C_6$ halocycloalkyl, $C_4$–$C_7$ cycloalkylalkyl, CHO, C(O)$R^{14}$, C(O)O$R^{14}$, C(S)$R^{14}$, C(S)S$R^{14}$, C(O)C(O)O$R^{14}$, C(O)$CH_2$C(O)O$R^{14}$, S(O)$_rR^{14}$, S(O)$_2CH_2$C(O)O$R^{14}$, P($X^1$)(O$R^{16}$)$_2$, S(O)$_rN(R^{11})$ C(O)O$R^{10}$, S(O)$_rN(R^{12})$ $R^{13}$, N=C$R^8R^9$, O$R^7$, N$R^7R^8$; benzyl substituted with 1–3 substituents independently selected from W; and $C_1$–$C_6$ alkyl substituted with 1–3 substituents independently selected from the group $C_1$–$C_3$ alkoxy, $C_1$–$C_3$ haloalkoxy, CN, $NO_2$, S(O)$_rR^{14}$, P($X^1$)(O$R^{16}$)$_2$, C(O)$R^{14}$, C(O)O$R^{14}$ and phenyl substituted with 1–3 substituents independently selected from W;

Z is O;

$R^1$ and $R^2$ are independently selected from the group H, halogen, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, O$R^7$, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, CN, $N_3$, SCN, $NO_2$, SH, S(O)$_rR^{14}$, OCHO, CHO, C(O)$R^{14}$, C(O)O$R^{14}$, C(O)N$R^{14}R^{15}$, S(O)$_2NR^{14}R^{15}$, N$R^{14}R^{15}$, N$R^{15}$C(O)$R^{14}$, OC(O)NH$R^{14}$, N$R^{15}$C(O)NH$R^{14}$, N$R^{15}$S(O)$_2R^{14}$, SF$_5$, phenyl substituted with 1–3 substituents independently selected from W, and benzyl substituted with 1–3 substituents independently selected from W; or when m or n is 2 and the two $R^1$ groups or the two $R^2$ groups are adjacent, ($R^1$)$_2$ or ($R^2$)$_2$ are taken together as —OCH$_2$O—, —OCF$_2$O—, —OCH$_2$CH$_2$O—, —CH$_2$C(CH$_3$)$_2$O—, —CF$_2$CF$_2$O— or —OCF$_2$CF$_2$O— to form a cyclic bridge;

$R^3$ is selected from the group J, H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_3$–$C_6$ cycloalkyl, $C_4$–$C_7$ cycloalkylalkyl, O$R^7$, $C_3$–$C_8$ alkoxycarbonylalkyl, CHO, C(O)$R^{14}$, C(O)O$R^{14}$, C(O)N$R^{14}R^{15}$, C(S) N$R^{14}R^{15}$, C(S)$R^{14}$, C(S)S$R^{14}$, CN, Si($R^{18}$) ($R^{19}$) ($R^{20}$), S(O)$_rR^{14}$, P($X^1$) (O$R^{16}$)$_2$, N$R^7R^8$, phenyl substituted with ($R^{21}$)$_p$, and benzyl substituted with 1–3 substituents independently selected from W; or $R^3$ is $C_2$–$C_6$ epoxyalkyl optionally substituted with 1–2 substituents independently selected from the group $C_1$–$C_3$ alkyl, CN, C(O)$R^{14}$, C(O)O$R^{14}$ and phenyl substituted with 1–3 substituents independently selected from W; or $R^3$ is $C_1$–$C_6$ alkyl substituted with 1–3 substituents independently selected from the group O$R^7$, C(O)N$R^{14}R^{15}$, C(O)$R^{14}$, S(O)$_rR^{14}$, SCN, CN, $C_1$–$C_2$ haloalkoxy, Si($R^{18}$) ($R^{19}$) ($R^{20}$) and N$R^7R^8$;

$R^4$ and $R^5$ are independently selected from the group H and $C_1C_4$ alkyl;

$R^6$ is selected from the group H, $C_1$–$C_4$ alkyl, $C_1$–$C_4$ haloalkyl, $C_2$–$C_4$ alkenyl, $C_2$–$C_4$ haloalkenyl, $C_2$–$C_4$ alkynyl, $C_2$–$C_4$ haloalkynyl, CHO, C(O)$R^{14}$, C(O) O$R^{14}$, C(O)N$R^{14}R^{15}$, C(S)N$R^{14}R^{15}$, C(S)$R^{14}$, C(S) S$R^{14}$, S(O)$_rR^{14}$, P($X^1$)(O$R^{16}$)$_2$, substituted phenyl, and substituted benzyl wherein the phenyl and benzyl substituents are 1–3 substituents independently selected from W;

$R^7$ is selected from the group H, $C_1$–$C_4$ alkyl, $C_1$–$C_4$ haloalkyl, $C_2$–$C_4$ alkenyl, $C_2$–$C_4$ haloalkenyl, $C_2$–$C_4$ alkynyl, $C_2$–$C_4$ haloalkynyl, C(O)$R^{14}$, C(O)O$R^{14}$, C(O)N$R^{14}R^{15}$, S(O)$_2NR^{14}R^{15}$, S(O)$_2R^{14}$, substituted phenyl, and substituted benzyl wherein the phenyl and benzyl substituents are 1–3 substituents independently selected from W;

$R^8$ is selected from the group H, $C_1$–$C_4$ alkyl, C(O)$R^{14}$ and C(O)O$R^{14}$;

$R^9$ is selected from the group H, $C_1$–$C_4$ alkyl, $C_1$–$C_4$ haloalkyl and phenyl substituted with 1–3 substituents independently selected from W; or $R^8$ and $R^9$ are taken together as (CH$_2$)$_4$ or (CH$_2$)$_5$;

$R^{10}$ is $C_1$–$C_{18}$ alkyl;

$R^{11}$ is $C_1$–$C_4$ alkyl;

$R^{12}$ and $R^{13}$ are independently $C_1$–$C_4$ alkyl; or $R^{12}$ and $R^{13}$ are taken together as (CH$_2$)$_4$, (CH$_2$)$_5$ or CH$_2$CH$_2$OCH$_2$CH$_2$;

$R^{14}$ is selected from the group $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, $C_4$–$C_7$ cycloalkylalkyl, substituted phenyl and substituted benzyl wherein the phenyl and benzyl substituents are 1-3 substituents independently selected from W;

$R^{15}$ is selected from the group H and $C_1$-$C_4$ alkyl; or $R^{14}$ and $R^{15}$, when attached to the same atom, are taken together as $(CH_2)_4$, $(CH_2)_5$ or $CH_2CH_2OCH_2CH_2$;

$R^{16}$ is selected from the group $C_1$-$C_3$ alkyl and phenyl substituted with 1-3 substituents independently selected from W;

$R^{18}$ and $R^{19}$ are independently $C_1$-$C_4$ alkyl;

$R^{20}$ is selected from the group $C_1$-$C_4$ alkyl and phenyl substituted with 1-2 substituents independently selected from W;

$R^{21}$ is selected from the group $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, OH, $OR^{14}$, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, halogen, CN, $N_3$, SCN, $SF_5$, $NO_2$, CHO, $C(O)R^{14}$, $C(O)OR^{14}$, $C(O)NR^{14}R^{15}$, $S(O)_rR^{14}$, $OC(O)R^{14}$, $OC(O)OR^{14}$, $OS(O)_2R^{14}$, $S(O)_2NR^{14}R^{15}$, $NR^{14}R^{15}$, $NR^{15}C(O)R^{14}$, $OC(O)NHR^{14}$, $NR^{15}C(O)NHR^{14}$, $NR^{15}S(O)_2R^{14}$, phenyl substituted with 1-3 substituents independently selected from W, and benzyl substituted with 1-3 substituents independently selected from W; or when p is 2 and the two $R^{21}$ groups are adjacent, $(R^{21})_2$ are optionally taken together as —$OCH_2O$—, —$OCF_2O$—, —$OCH_2CH_2O$—, —$CH_2C(CH_3)_2O$—, —$CF_2CF_2O$— or —$OCF_2CF_2O$— to form a cyclic bridge;

J is selected from the group

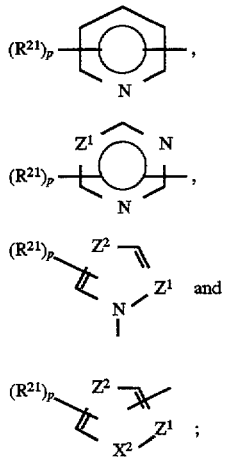

W is selected from the group H, halogen, CN, $NO_2$, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfonyl, and $C_1$-$C_2$ haloalkylsulfonyl;

$X^2$ is selected from the group O and S;

$Z^1$ and $Z^2$ are independently selected from the group CH and N;

m is 1 to 3;

n is 1 to 3;

p is 0 to 3; and r is 0, 1 or 2.

2. A compound according to claim 1 wherein

Y is selected from the group H, $C_1$-$C_6$ alkyl, $C(O)R^{14}$ and $C(O)OR^{14}$.

3. A compound according to claim 2 wherein $R^3$ is selected from the group $C_1$-$C_4$ alkyl, $C(O)OR^{14}$ and phenyl substituted with $(R^{21})_p$; and X is O.

4. A compound according to claim 3 wherein $R^1$ is selected from the group $C_1$-$C_2$ haloalkyl, $C_1$-$C_2$ haloalkoxy and halogen;

$R^2$ is selected from the group H, $C_1$-$C_2$ haloalkyl, $C_1$-$C_2$ haloalkoxy and halogen;

m is 1; and n is 1.

5. A compound according to claim 4 wherein

A and E are taken together to form $CH_2$ and $OCH_2$.

6. A compound according to claim 4 wherein

A is H; and

E is H; and $R^2$ is in the meta postion.

7. A compound according to claim 6 which is:

4-(3-chlorophenyl)-5,6-dihydro-5-phenyl-N-[4-(trifluoromethoxy)phenyl]-4H-1,3,4-oxadiazine-2-carboxamide.

8. An arthropodicidal composition comprising an arthropodicidally effective amount of a compound according to claim 1 and a carrier therefor.

9. A method for controlling arthropods comprising contacting the arthropods or their environment with an arthropodicidally effective amount of a compound according to claim 1.

* * * * *

UNITED STATES PATENT AND TRADEMARK OFFICE
CERTIFICATE OF CORRECTION

PATENT NO. : 5,728,693
DATED : March 17, 1998
INVENTOR(S) : Stevenson

It is certified that error appears in the above-identified patent and that said Letters Patent is hereby corrected as shown below:

Column 11, line 34 delete "whim" and substitute therefor --which--.

Column 21, Index Table A, compound 17, column 2 delete "OCK$_3$" and substitute therefor "OCF$_3$".

Column 22, Index Table A, line 18 delete "4.3 (m, 1H)" and substitute therefor "4.2 (m, 1H)".

Column 22, Index Table A, line 20 delete "4.7 (m, 1H)".

Signed and Sealed this

Twenty-third Day of March, 1999

Attest:

Q. TODD DICKINSON

Attesting Officer     Acting Commissioner of Patents and Trademarks